(12) United States Patent
Anderegg et al.

(10) Patent No.: US 9,389,156 B2
(45) Date of Patent: Jul. 12, 2016

(54) METHOD FOR DETERMINING THE STIFFNESS AND/OR DAMPING OF AN AREA OF A PHYSICALNESS

(75) Inventors: Roland Anderegg, Olten (CH); Martin Gerhard, Niederrohrdorf (CH); Kuno Kaufmann, Subingen (CH)

(73) Assignee: Ammann Schweiz AG, Langenthal (CH)

( * ) Notice: Subject to any disclaimer, the term of this patent is extended or adjusted under 35 U.S.C. 154(b) by 755 days.

(21) Appl. No.: 13/879,109

(22) PCT Filed: Oct. 13, 2010

(86) PCT No.: PCT/CH2010/000254
§ 371 (c)(1),
(2), (4) Date: Jun. 18, 2013

(87) PCT Pub. No.: WO2012/048433
PCT Pub. Date: Apr. 19, 2012

(65) Prior Publication Data
US 2013/0261998 A1    Oct. 3, 2013

(51) Int. Cl.
*G01N 11/00*    (2006.01)
*G01N 3/32*    (2006.01)
*E01C 19/28*    (2006.01)

(52) U.S. Cl.
CPC ................ *G01N 3/32* (2013.01); *E01C 19/288* (2013.01)

(58) Field of Classification Search
CPC ......... E01C 19/288; E02D 1/00; E02D 3/026; G01N 3/32; G01N 33/24; G01N 19/00; G01N 17/00; G01N 3/00
See application file for complete search history.

(56) References Cited

U.S. PATENT DOCUMENTS

| 6,431,790 B1* | 8/2002 | Anderegg | ............. | E01C 19/288 366/116 |
| 8,671,760 B2* | 3/2014 | Wallrath | ............... | E01C 19/288 73/584 |
| 9,169,605 B2* | 10/2015 | Corcoran | ................ | E01C 19/26 |

FOREIGN PATENT DOCUMENTS

| EP | 1516961 A1 | 3/2005 |
| WO | 2007096118 A1 | 8/2007 |

OTHER PUBLICATIONS

International search report for PCT/CH2010/000254 dated Jul. 15, 2011.

*Primary Examiner* — An Do
(74) *Attorney, Agent, or Firm* — McCormick, Paulding & Huber LLP

(57) ABSTRACT

The invention relates to a method for determining the soil stiffness ($k_B$) of a soil area (2). For this purpose, a vibration-excited contact body (6, 8) of a soil compacting device (1) acts upon the soil surface (9) in such a way that during the acting upon an unsteady loss of contact (jumping) between the soil surface (9) and the contact body (6, 8) occurs. While acting upon the soil surface, parameters (f) of the oscillation excitation and parameters ($\ddot{x}_d$) of the oscillation response ($x_d$) of the contact body (6, 8) are determined and from these in combination with known parameters ($m_u$, $r_u$, $m_d$) of the soil compacting device (1) the soil stiffness ($k_B$) is computed.

23 Claims, 1 Drawing Sheet

METHOD FOR DETERMINING THE STIFFNESS AND/OR DAMPING OF AN AREA OF A PHYSICALNESS

CROSS REFERENCE TO RELATED APPLICATIONS

This application claims the priority of PCT Application No. PCT/CH2010/000254, filed on Oct. 13, 2010, the disclosure of which is incorporated herein by reference in its entirety.

TECHNICAL FIELD

The invention concerns a method for determining the stiffness and/or damping of an area of a physicalness and an apparatus for performing the method according to the preambles of the independent claims.

BACKGROUND ART

Generally it is known that in systems which are able to perform oscillations, the stiffness and the damping of a connection that allows oscillations can be computed when the oscillation excitation and the oscillation response are known.

In the field of soil compaction, this possibility is used to compute, from known parameters of the compaction machine and from parameters of the oscillation excitation of the unbalance type vibrator of the machine and of the oscillation response of the contact body (roller or bottom plate) of the machine, which are determined during compaction operation, the soil stiffness, and thereby be in position to draw conclusions with regard to the degree of compaction of the soil.

However, due to the unidirectional linking between the soil and the contact body of the compacting machine there arises the problem that, depending on the soil stiffness and the mode of operation of the compacting machine, three different operating conditions can occur.

In a first condition, which is also termed "contact operation", during acting upon the soil with the contact body there exists at any time a contact between the contact body and the soil.

In a second condition, which is also termed "periodical loss of contact", during acting upon the soil with the contact body it occurs in uniform intervals a contact loss between the contact body and the soil.

In a third condition, which is also termed "jumping", during acting upon the soil with the contact body it occurs in unsteady intervals a contact loss between the contact body and the soil.

The three before described operation conditions can generally occur in all systems which are able to perform oscillations and are having an unidirectional linking.

SUMMARY OF THE INVENTION

Since so far it has been considered impossible to compute the stiffness from parameters which have been determined in the operating condition of jumping, the determination of the soil stiffness during compaction was limited to the operation conditions "contact operation" and "periodical loss of contact", and thereby to expensive, regulated compacting machines, which by their control system automatically are run in the last mentioned operation conditions and allow no jumping.

Surprisingly it has now been found that for systems which are able to perform oscillations and having an unidirectional linking, a computation of the stiffness and the damping is also possible from parameters of the oscillation excitation and the oscillation response which have been determined in the operating condition of jumping. By this, in the field of soil compaction there arises now the possibility to reliably determine the soil stiffness in all operating conditions, so that it becomes meaningful to also equip unregulated compacting machines, like e.g. simple vibratory plate compactors, which in operation oftentimes experience the condition of jumping, with corresponding measuring and computation electronics.

A first aspect of the invention concerns a method for determining the stiffness and/or damping of an area of a physicalness, like e.g. of a soil that is compacted or shall be compacted or of a building wall that shall be drilled through. In the field of soil compaction, the knowledge of the soil stiffness or of the soil damping, respectively, is desirable since it allows to draw conclusions regarding the loading capacity and the degree of compaction of the soil, respectively, and therewith helps to avoid constructional defects and unnecessary work. In the field of drilling technics, the knowledge of the stiffness or the damping, respectively, of the wall area that is currently treated with the drill is desirable since it allows to draw conclusions regarding its material and thereby, e.g. by means of a suitable alarm or control system, respectively, can help to avoid an unintended drilling of pipes running inside that wall.

According to the method according to the invention, a contact body is excited by means of an unbalance type vibrator to perform oscillations, and with the contact body that is excited to perform oscillations it is acted upon a contact surface of the area, the stiffness and/or damping of which shall be determined, in a direction substantially perpendicular to the contact surface. In doing so, the oscillation excitation by means of the unbalance type vibrator is such that due to this oscillation excitation during the acting upon the contact surface an unsteady contact loss between the contact surface and the contact body occurs. Thus, during the acting upon the contact surface it comes to a "jumping" of the contact body on the contact surface. In this operational condition the parameters of the oscillation excitation of the unbalance type vibrator and of the oscillation response of the contact body are determined and subsequently the stiffness and/or damping of the area is computed from the parameters of the oscillation excitation of the unbalance type vibrator and of the oscillation response of the contact body determined in this way and from known parameters of the system unbalance type vibrator—contact body.

In a preferred embodiment of the method, the acting upon the contact surface is performed substantially in direction of gravity, i.e. the gravity acts substantially perpendicular to the contact surface. This has the advantage that the contact body, without the help of additional forces that act perpendicular to the contact surface, always automatically comes back into contact with the contact surface.

In a further preferred embodiment of the method, a tool is used as contact body, by means of which the area, the stiffness and/or damping of which shall be determined, during the acting upon is treated, namely in particular is compacted (e.g. soil compaction) or broken up (e.g. drilling). By this, the advantage is arrived at that a treatment takes place simultaneously with the determining of the stiffness and/or the damping, and that the intensity of the treatment can be set in dependency of the determined stiffness or damping values, respectively.

In still a further preferred embodiment of the method, the unbalance type vibrator, during the determining of the parameters of the oscillation excitation of the unbalance type vibrator and of the oscillation response of the contact body, is operated in such a manner that the oscillation excitation of the contact body is substantially constant. This is accomplished very easy by using an unregulated unbalance type vibrator and makes possible the cost efficient provision of suitable apparatuses for performing the method according to the invention.

Preferably, the acting upon the contact surface with the contact body takes place in such a manner that, due to the oscillation excitation of the unbalance type vibrator, during the acting upon temporarily a steady contact loss occurs, thus the operation condition "periodical loss of contact" occurs, and/or no contact loss between the contact surface and the contact body occurs, thus the operation condition "contact operation" occurs. In particular in the field of soil compaction, this embodiment is especially advantageous, since in this way the stiffness or damping is determined in all possible operation conditions.

Also it is preferred that as parameters of the oscillation excitation and of the oscillation response a rotational pulse of the unbalance type vibrator and the course of the acceleration of the contact body are determined, and that from these parameters together with known parameters of the system unbalance type vibrator—contact body, like e.g. the mass of the unbalance type vibrator, the distance of the mass center of the unbalance mass from the center of rotation and the mass of the contact body, the stiffness and/or damping of the area of the physicalness, onto which is acted upon, is determined.

In doing so, preferably the oscillation response of the contact body is determined by two times integrating the determined acceleration of the contact body, and subsequently from this the portion of the excitation frequency of the oscillation response of the contact body is determined by filtering or FFT-analysis, respectively. It has been found that based on this portion of the excitation frequency of the oscillation response of the contact body, a computation of the stiffness and the damping is possible also in the operation condition of jumping.

For doing so, according to a first preferred variant of the method, the amplitude of the portion of the excitation frequency of the oscillation response of the contact body and the phase lag of this portion with respect to the oscillation excitation are determined and subsequently, with the knowledge of the mass of the contact body, of the mass of the unbalance, of the distance of the mass center of the unbalance mass from the center of rotation as well as of the excitation frequency, the soil stiffness $k_B$ is computed according to or with the involvement of the following formula:

$$k_B = 4\pi^2 f^2 \left(m_d + \frac{m_u r_u \cos\varphi}{A_1}\right)$$

Therein f is the excitation frequency, $m_d$ is the mass of the contact body, $m_u$ is the mass of the unbalance, $r_u$ is the distance of the mass center of the unbalance mass from the center of rotation, $\varphi$ is the phase lag of the portion of the excitation frequency of the oscillation response of the contact body with respect to the oscillation excitation and A1 is the amplitude of the portion of the excitation frequency of the oscillation response of the contact body.

In another preferred variant of the method, before the computation of the stiffness and/or damping, first the ratio of the dynamic forces acting in opposite direction than the gravity forces to the weight forces acting in direction of the gravity forces is determined from determined parameters of the oscillation excitation of the unbalance type vibrator and/or of the oscillation response of the contact body and from known parameters of the acting upon arrangement. In dependency of this ratio different formulas are then applied for the computation of the stiffness and/or the damping. This variant of the method provides the advantage that it allows the consideration of specific factors which are subject to changes in dependency of this ratio, like e.g. the influence of deeper soil layers in the case of soil compaction, and thereby in particular for the operation conditions "periodical loss of contact" and "jumping" makes possible a more precise computation than the first variant.

Preferably, for doing so the amplitude of the portion of the excitation frequency of the oscillation response of the contact body and the phase lag of the portions of the excitation frequency of the oscillation response of the contact body with respect to the oscillation excitation are determined. Thereafter, with the knowledge of the mass of the contact body, of the mass of the unbalance, of the distance of the mass center of the unbalance mass from the center of rotation, of the mass that acts through the chassis frame upon the roller body as well as of the excitation frequency, a characteristic value $\phi$ is computed according to or with the involvement of the following formula, which characteristic value puts into relation the dynamic forces acting in opposite direction than the gravity to the weight forces acting in direction of gravity:

$$\Phi = \frac{4\pi^2 f^2 m_u r_u \sqrt{\left(\frac{A_1}{A_0}\right)^2 + 1 + 2\left(\frac{A_1}{A_0}\right)\cos\varphi}}{(m_f + m_d)g}$$

Therein f is the excitation frequency, $m_u$ is the mass of the unbalance, $r_u$ is the distance of the mass center of the unbalance mass from the center of rotation, $\varphi$ is the phase lag of the portion of the excitation frequency of the oscillation response of the contact body with respect to the oscillation excitation, A1 is the amplitude of the portion of the excitation frequency of the oscillation response of the contact body, $m_f$ is the mass acting upon the roller body through the chassis frame, $m_d$ is the mass of the contact body and g the gravity acceleration.

The parameter $A_0$ is computed according to or with involvement of the following formula:

$$A_0 = \frac{m_u r_u}{m_d}$$

A characteristic value $\phi$ computed in such way has proven especially suitable in the field of soil compaction machinery, in particular in cases in which, when the characteristic value $\phi$ is less than 1, a different formula is used for the computation of the stiffness and/or damping than when the characteristic value $\phi$ is greater than 1.

When the characteristic value $\phi$ is less than 1, the stiffness preferably is computed according to the formula of the first variant of the method.

When the characteristic value $\phi$ is greater than 1, the stiffness preferably is computed according to or with involvement of the following formula:

$$k_B = \frac{4\pi^2 f^2 (A_1 m_d + m_u r_u \cos\varphi)}{A_1 \left(1 + \cos\left\{\frac{\pi}{2}\left(\frac{\Phi-1}{1,14}\right)^K\right\}\right)}$$

Therein f is the excitation frequency, $m_u$ is the mass of the unbalance, $r_u$ is the distance of the mass center of the unbalance mass from the center of rotation, $\phi$ is the phase lag of the portion of the excitation frequency of the oscillation response of the contact body with respect to the oscillation excitation, A1 is the amplitude of the portion of the excitation frequency of the oscillation response of the contact body, $m_d$ is the mass of the contact body and K is an empirical factor between 0.3 and 0.5.

By advantage, for different sizes of the characteristic values $\phi$ different empirical factors K are employed, namely preferably when the characteristic values $\phi$ is between 1 and 2, a first empirical factor K is used and when the characteristic values $\phi$ is greater than 2.5, an empirical factor K is used which is smaller than the first empirical factor K. In the field of soil compacting machinery is has for example proven advantageous to use a factor K of 0.45 when the characteristic value $\phi$ is between 1 and $\pi-1$ (2.1415) and to use a factor of 0.36 when the characteristic value $\phi$ is greater than $\pi-1$ (2.1415).

In a further preferred embodiment, beside the portion of the excitation frequency of the oscillation response of the contact body, in addition a determination for possibly present portions of other frequencies of the oscillation response of the contact body, which are lower than the excitation frequency, in particular which are fractions of the excitation frequency f (e.g. f/2, f/3, f/4, etc.) is performed. If such portions of substantial size are determined, in dependency of the result of the determination the computation of the stiffness and/or the damping is influenced, e.g. by adapting a correction factor in a formula or by canceling the computation.

In case for example that a substantial portion of the natural frequency of a mass that is coupled to the contact body in a manner that it can oscillate in acting upon direction and/or a substantial portion of a frequency which in the sense of period duplication is not subharmonic and is lower than the excitation frequency f (e.g. f/3, f/5, etc.) is determined, this indicates that there is a chaotic oscillation state and it is preferred that in this case a control intervention with respect to the unbalance type vibrator is performed in order to establish a permissible operational state and/or no computation of the stiffness and/or damping is performed, since then the results of the computation would be wrong.

Further it is in the method according to the invention preferred that the parameters of the oscillation excitation of the unbalance type vibrator and of the oscillation response of the contact body are continuously determined and continuously the stiffness and/or the damping of the area of the physicalness, onto which is acted upon, is computed from these parameters. By this, in particular in embodiments of the method in which the contact surface during the acting upon at the same time is treated, the advantage is arrived at that a monitoring of the result of the treatment and/or of the basic conditions of the treatment becomes possible.

In still a further preferred embodiment of the method, the determined stiffness and/or damping is made noticeable, in particular made visually noticeable, which preferably is accomplished in that it is displayed as numerical value or as bar of variable size. Through this, it is possible for a person performing the method to recognize the absolute or relative magnitude of the determined stiffness and/or damping and if necessary to change in dependency thereof certain parameters of the method or to stop performance of the method. Of course, it is also intended to make in addition other parameters and process values noticeable, in particular visually noticeable, like e.g. the maximum contact surface reaction force or the rotational frequency of the unbalance type vibrator.

Especially preferred are embodiments of the method in which by means of the bottom plate of a vibratory plate compactor or with the roller body of a vibratory roller as contact body it is acted upon the surface of a soil, which preferably is compacted and/or shall be compacted, and the soil stiffness and/or damping of the soil area is computed. In such embodiments, the advantages of the method according to the invention become especially clear apparent, since the soil stiffness or the soil damping, respectively, allow conclusions regarding the degree of compaction of the soil, whereby e.g. an inadequate soil compaction can be detected or e.g. unnecessary compaction work can be avoided.

In the before described embodiment, the invention thus concerns a method for determining the soil stiffness and/or soil damping of a soil area, in which by means of a vibration-excited contact body of a soil compaction apparatus it is acted upon the surface of the soil in such a manner, that during the acting upon it comes to an unsteady contact loss between the surface of the soil and the contact body. During this acting upon the surface, parameters of the oscillation excitation and parameters of the oscillation response of the contact body are determined and from these in combination with known parameters of the soil compacting apparatus the soil stiffness and/or the soil damping is computed.

Preferably, the bottom plate of the vibratory plate compactor or the roller body of the vibratory roller during the acting upon the surface is moved along the surface of the soil area. This is in particular of advantage in embodiments of the method in which continuously the soil stiffness and/or the soil damping is determined, since by doing so the soil stiffness or soil damping profile of a relative large soil area can be determined.

Also it is preferred that the soil area during the acting upon its surface with the bottom plate of the vibratory plate compactor or with the roller body of the vibratory roller is compacted. By means of this, it becomes possible to perform compaction work and, at the same time, to check the compaction result.

A second aspect of the invention concerns an apparatus for performing the method according to the first aspect of the invention. The apparatus comprising a contact body for acting upon a contact surface of the area, the stiffness and/or damping of which shall be determined, in a direction substantially perpendicular to the contact surface as well as an unbalance type vibrator, by means of which the contact body can be excited to perform oscillations in such a manner that, during the intended acting upon the contact surface, due to this oscillation excitation it comes or it can come to an unsteady contact loss (jumping) between the contact surface and the contact body. The unbalance type vibrator preferably is an unregulated unbalance type vibrator, since such unbalance type vibrators are inexpensive and sturdy.

Further, the apparatus comprises measuring means for a determination of parameters of the oscillation excitation of the unbalance type vibrator (e.g. rotational pulse) and of parameters of the oscillation response of the contact body (e.g. course of acceleration of the contact body in the direction of the acting upon) during an acting upon the contact surface while an unsteady contact loss between the contact surface and the contact body occurs.

The apparatus also comprises computing means for a computation of the stiffness and/or damping of the area of the physicalness from the parameters of the oscillation excitation of the unbalance type vibrator and of the oscillation response of the contact body which have been determined during the acting upon the contact surface while an unsteady contact loss (jumping) occurred between the contact surface and the contact body.

Preferably, the measuring means and the computing means are designed in such a manner that a continuous determination of the parameters of the oscillation excitation of the unbalance type vibrator and of the oscillation response of the contact body and a continuous computation of the stiffness and/or damping of the area of the physicalness can be carried out.

In a preferred embodiment of the apparatus, the measuring means and the computing means are designed in such a manner that in addition they are suitable for a determination of the parameters and for a computation of the stiffness and/or damping during an acting upon the contact surface while a steady contact loss (periodical loss of contact) and/or while no contact loss (contact operation) between the contact surface and the contact body occurs. Thus, the stiffness and/or the damping can be determined in all operational states which can occur during the intended operation of the apparatus.

Also it is preferred that the apparatus comprises means for making the determined stiffness and/or damping visually noticeable. For doing so, by advantage it comprises a display on which a numeric value representing the stiffness and/or damping is displayed or a bar, the lengths of which represents the stiffness and/or damping. By means of this, the operator can read the absolute or relative magnitude of the stiffness and/or damping at the machine and can, if necessary, influence operational parameter of the machine in dependence therefrom or stop the operation of the machine. Furthermore it is also envisaged to equip the apparatus with means for making visually noticeable other parameters and process values, like e.g. the maximum contact surface reaction force or the rotational frequency of the unbalance type vibrator.

Generally it is also envisaged to equip the apparatus with means for performing further functions, like e.g. data acquisition, storage of data, data backup, data analysis and data transfer (e.g. interface against the outside CAN-bus), and in case of soil compaction applications e.g. also with a position determination function via GPS. By this the documentation and analysis of the determined stiffness and/or damping values together with dedicated data can be facilitated or automated, respectively.

In a further preferred embodiment of the apparatus, the contact body is formed by a tool for treating the area of the physicalness. Thus, the apparatus is a machine for treating the contact surface, namely preferably a vibratory plate compactor or a vibratory roller, the bottom plate or roller body of which forms the contact body. At such apparatuses, the advantages of the invention become especially clearly apparent.

Further, it is preferred that the unbalance type vibrator of the apparatus is a circular vibrator or a directional vibrator, preferably a directional vibrator with adjustable exciting force direction.

BRIEF DESCRIPTION OF THE DRAWINGS

Further embodiments, advantages and applications of the invention result from the dependent claims and from the following description on the basis of the drawings. Therein show:

DESCRIPTION OF THE PREFERRED EMBODIMENTS

Figure 2:
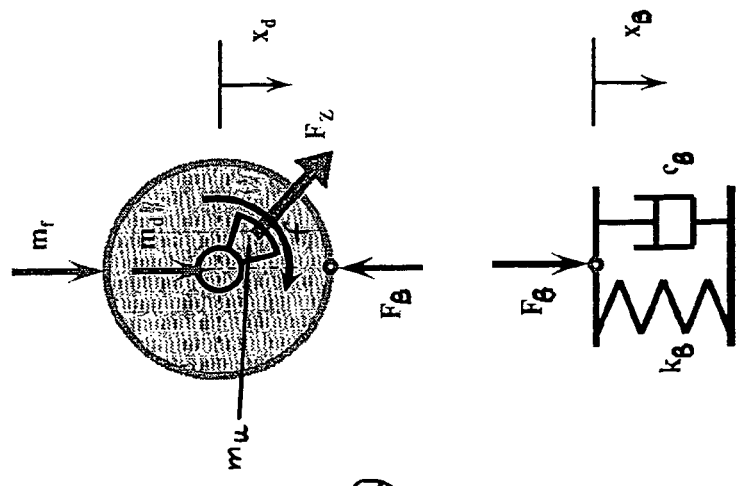
FIG. 2 the vibration engineering model of the oscillating system formed by the single drum roller and the soil of FIG. 1.
Figure 1:
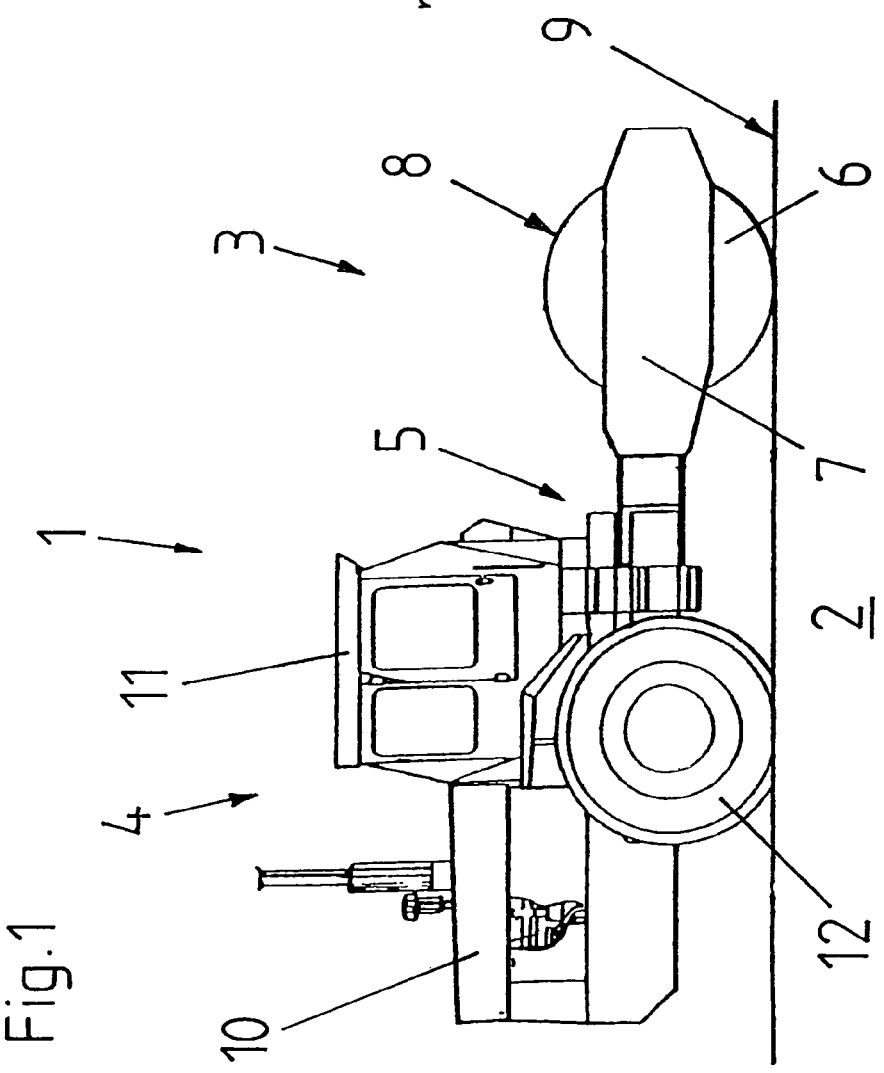
FIG. 1 a side view of a single drum roller for soil compaction.

FIG. 1 shows an apparatus according to the invention in the form of a single drum roller 1 for soil compaction in the side view and FIG. 2 schematically the vibration engineering model of the oscillating system that is formed by the single drum roller 1 and the soil 2 arranged under the roller 6 thereof.

As is visible here, the single drum roller 1 has a front part 3 and a rear part 4, which are connected to each other via an articulated joint 5.

The front part 3 of the single drum roller 1 substantially consists of a roller body 6 and a chassis frame 7.

The roller body 6 encompasses a drum 8 (contact body according to the claims), which stands on the surface 9 (contact surface according to the claims) of the soil 2 that shall be compacted. Inside the drum 8 there is arranged an unbalance type vibrator (not shown) of the circular vibrator type which can be driven by a hydraulic motor and by which the drum 8 can be excited to perform oscillations in such manner that it comes to an unsteady contact loss (jumping) between the drum 8 and the surface of the soil 9.

The chassis frame 7 rests in direction of gravity forces on the two end-sided bearings of the roller body 6 and via connecting elements, which isolate the oscillations, is connected with the articulated joint 5, which is carried by the rear part 4 of the single drum roller. The connecting elements which isolate the oscillations are designed in such a manner that the rear part 4 of the single drum roller together with the chassis frame 7 forms a mechanically interconnected unit but with regard to oscillations is isolated therefrom.

The rear part 4 of the single drum roller substantially consists of a hydraulic unit 10 with a diesel engine, which drives a hydraulic pump, and a driving cab 11. It rests by means of two drive wheels 12 which are driven by two hydraulic motors on the soil 2. In operation, the hydraulic pump supplies, via hydraulic hoses, the hydraulic motor of the unbalance type vibrator of the roller body 6 as well as the hydraulic motors of the drive wheels 12 in each case with a stream of pressurized hydraulic fluid, for driving the drive wheels 12 and the unbalance type vibrator of the roller body 6.

In the vibration engineering model according to FIG. 2, the mass of the roller body 6, i.e. of the drum 8 with the unbalance type vibrator arranged therein, is designated by $m_d$, the mass acting via the chassis frame 7 onto the roller body 6 by $m_f$, the unbalance mass of the unbalance type vibrator by $m_u$, the centrifugal force generated by the unbalance mass $m_u$ by $F_Z$, the soil reaction force acting upon the surface 9 of the soil 2 by $F_B$, the stiffness of the soil 2 by $k_B$, the damping of the soil 2 by $c_B$, the movement of the drum 8 in vertical direction (perpendicular to the soil surface 9) by $x_d$, the movement of the surface 9 of the soil 2 in vertical direction by $x_B$ and the rotational frequency of the unbalance mass of the unbalance type vibrator by f.

Further, the single drum roller 1 is equipped with means for continuously determining the rotational frequency f of the unbalance mass $m_u$ of the unbalance type vibrator (parameter of the unbalance excitation of the unbalance type vibrator) and the acceleration $\ddot{x}_d$ of the drum 8 of the roller body 6 in vertical direction (parameter of the oscillation response of the contact body), as well as with a computation unit, by means of which from these two determined parameters together with known parameters of the single drum roller 1 continuously the soil stiffness $k_B$ and the soil damping $c_B$ can be computed. The determined data are made visually noticeable at the control panel of the single drum roller 1 and depending on the equipment are documented and saved. Optionally, a GPS-system is available by means of which these data together with other machine data can be documented in a accurate manner with respect to place and time.

The determination of the before mentioned parameters and the computation of the soil stiffness $k_B$ and of the soil damping $c_B$ is possible in the three operation conditions contact operation, periodical loss of contact and jumping, in standstill operation as well as in moving operation.

In the simple most case, this is accomplished as follows: Within the unbalance type vibrator with each rotation of the unbalance shaft a pulse is generated by means of a pulse sensor, the tact of which corresponds to the rotational frequency f of the unbalance mass $m_u$. By means of an acceleration sensor arranged at one bearing block of the roller body 6, the course of the acceleration $\ddot{x}_d$ of the drum 8 in vertical direction in the form of a voltage signal is determined.

This voltage signal is digitalized and two times integrated, so that the course in time and the magnitude of the oscillation movement $x_d$ of the drum 8 is obtained. This course represents the oscillation response $x_d$ of the oscillating system to the oscillation excitation of the unbalance type vibrator.

From the course of the oscillation movement $x_d$ of the drum 8 obtained in this manner, by means of FFT-analysis or filtering, respectively, the course in time of the portion of the excitation frequency f of the oscillation response $x_d$ of the drum 8 and the amplitude A1 thereof is determined.

From the knowledge of the installation position of the pulse sensor and the angular position, in which the unbalance weight of the unbalance type vibrators at the point in time of the pulse is positioned, the course in time of the exciting force of the unbalance type vibrator is determined. Through a comparison of the course in time of the excitation force with the course in time of the portion of the excitation frequency f of the oscillation response $x_d$ of the drum 8 the phase lag $\varphi$ of the portion of the excitation frequency f of the oscillation response $x_d$ of the drum 8 with respect to the oscillation excitation of the unbalance type vibrator is then determined. With the knowledge of the mass $m_f$ that is acting from the chassis frame onto the roller body 6, of the mass $m_d$ of the roller body 6, of the mass $m_u$ of the unbalance, of the distance of the mass center $r_u$ of the unbalance mass from the center of rotation as well as of the excitation frequency f, the soil stiffness $k_B$ can now be computed with satisfactory accuracy for the three operation conditions contact operation, periodical loss of contact and jumping according to or with involvement of the following formula:

$$k_B = 4\pi^2 f^2 \left(m_d + \frac{m_u r_u \cos\varphi}{A_1}\right)$$

In case a more precise determination of the soil stiffness $k_B$ in the three operation conditions contact operation, periodical loss of contact and jumping is desired, a characteristic value $\phi$ is formed according to or with the involvement of the following formula which puts into ration the dynamic forces acting opposite to the direction of the gravity to the weight forces acting in direction of gravity:

$$\Phi = \frac{4\pi^2 f^2 m_u r_u \sqrt{\left(\frac{A_1}{A_0}\right)^2 + 1 + 2\left(\frac{A_1}{A_0}\right)\cos\varphi}}{(m_f + m_d)g}$$

Therein, the parameter $A_0$ is computed according to or with involvement of the following formula:

$$A_0 = \frac{m_u r_u}{m_d}$$

In case the characteristic value $\phi$ is less than 1, the weight forces are larger than the forces acting periodically against the direction of gravity and contact operation is the operation condition. In this case the soil stiffness $k_B$ is computed with the before described formula.

In case the characteristic value $\phi$ is greater than 1, the weight forces are smaller than the forces acting periodically against the direction of gravity and the operation condition is periodical loss of contact or jumping.

If in that case the characteristic value $\phi$ is bigger than 1 but smaller than $\pi-1$ (2.1415), the soil stiffness $k_B$ is computed according to or with the involvement of the following formula:

$$k_B = \frac{4\pi^2 f^2 (A_1 m_d + m_u r_u \cos\varphi)}{A_1 \left(1 + \cos\left\{\frac{\pi}{2}\left(\frac{\Phi-1}{1,14}\right)^{0,45}\right\}\right)}$$

If however the characteristic value $\phi$ is larger than $\pi-1$ (2.1415), the soil stiffness $k_B$ is computed according to or with the involvement of the following formula:

$$k_B = \frac{4\pi^2 f^2 (A_1 m_d + m_u r_u \cos\varphi)}{A_1 \left(1 + \cos\left\{\frac{\pi}{2}\left(\frac{\Phi-1}{1,14}\right)^{0,36}\right\}\right)}$$

The two last mentioned formulas consider the influence of deeper soil layers on the oscillation response $x_d$ of the drum 8, which at periodical loss of contact is increasing, by means of empirical factors (factor K according to the claims). In the present case, these are the exponents 0.45 and 0.36, respectively, in the before mentioned formulas.

Since with compaction machines which allow the operation condition periodical loss of contact or jumping, respectively, it can come under certain conditions to chaotic oscillation situations, in which the oscillation response has no periodicity at all and a determination of the soil stiffness with the given formulas, which assume linearity or the validity of the scenario of period duplication, respectively, is not possible, it is envisaged here that optionally the oscillation response $x_d$ of the drum 8 by suitable filtering or FFT-analysis, respectively, is checked in order to find out if oscillation portions of the natural frequency $f_0$ of the structure of the remaining single drum roller that is coupled via the chassis frame 7 to the roller body 6 and/or other low frequency oscillation portions, e.g. the frequency f/3, are contained in the oscillation response $x_d$ of the drum 8 to a substantial extend. The natural frequency $f_0$ of the structure of the remaining single drum roller that is coupled via the chassis frame 7 to the roller body 6 can be determined by measurements.

In case such oscillation portions are detected, no computation of the soil stiffness $k_B$ is carried out and at the control panel it is signalized that an unacceptable operation condition exists which has to be eliminated. In a preferred embodiment, the single drum roller 1 in case of the occurring of such operation conditions is automatically brought back into one of the three admissible operating conditions contact operation, periodical loss of contact or jumping, since a chaotic operation condition within short time can damage or even destroy the single drum roller.

The soil damping $c_B$ can be determined from the determined soil stiffness $k_B$ and the before mentioned parameters according to or with involvement of the following formula:

$$c_B = k_B \frac{1}{2\pi f} \tan\left\{\arccos\left(\frac{(\Delta F_B)^2 + (m_d \Omega^2 A_1)^2 - (m_u r_u \Omega^2)^2}{2 m_d \Omega^2 A_1 \Delta F_B}\right)\right\}$$

Therein, the parameters $\Delta F_B$ and $\Omega$ are determined according to or with the involvement of the following formulas, wherein g is the acceleration of gravity:

$$\Delta F_B = \Phi(m_f + m_d)g$$

$$\Omega = 2\pi f$$

While there are described in the present application preferred embodiments of the invention it is to be pointed our that the invention is not limited thereto but may be otherwise variously embodied and practised within the scope of the following claims. In particular it is to be pointed out that the method for computing the stiffness and damping values which is described here on the basis of a single drum roller according to the invention can also be performed with other machines according to the invention, for example with vibratory plate compactors or drilling machines according to the invention.

The invention claimed is:

1. Method for determining the stiffness ($k_B$) and/or damping ($c_B$) of an area of a physicalness (2), in particular for determining the soil stiffness ($k_B$) and/or the soil damping ($c_B$) of a soil area, comprising the steps:
   a) providing an acting upon arrangement (1) comprising a contact body (6, 8) and an unbalance type vibrator, by means of which the contact body (6, 8) can be excited in order to perform oscillations ($x_d$);
   b) acting upon a contact surface (9) of the area, the stiffness ($k_B$) and/or the damping ($c_B$) of which shall be determined, by means of the contact body (6, 8) in a direction which runs substantially perpendicular to the contact surface (9), wherein the contact body (6, 8) by the unbalance type vibrator is excited to perform oscillations ($x_d$), such that due to this oscillation excitation during the acting upon the contact surface an unsteady contact loss between the contact surface (9) and the contact body (6, 8) occurs;
   c) determining of parameters (f, $\ddot{x}_d$) of the oscillation excitation of the unbalance type vibrator and of the oscillation response of the contact body (6, 8) during the acting upon the contact surface (9) while an unsteady contact loss occurs; and
   d) computing the stiffness ($k_B$) and/or the damping ($c_B$) of the area from the parameters (f, $\ddot{x}_d$) of the oscillation excitation of the unbalance type vibrator and of the oscillation response of the contact body which have been determined during the acting upon the contact surface while an unsteady contact loss occurred and from known parameters ($m_u$, $r_u$, $m_d$) of the acting upon arrangement (1), wherein as parameters (f, $\ddot{x}_d$) of the oscillation excitation and of the oscillation response a rotational pulse (f) of the unbalance type vibrator and the course of the acceleration ($\ddot{x}_d$) of the contact body (6, 8) in the direction of acting upon the contact surface are determined and from these parameters (f, $x_d$) together with known parameters ($m_u$, $r_u$, $m_d$) of the system unbalance type vibrator—contact body, the stiffness ($k_B$) and/or the damping ($c_B$) is computed, and wherein the oscillation response ($x_d$) of the contact body (6, 8) is determined by two times integrating the determined acceleration ($\ddot{x}_d$) of the contact body (6, 8) in the direction of acting upon the contact surface and the portion of the excitation frequency (f) of the oscillation response ($x_d$) of the contact body (6, 8) is determined.

2. Method according to claim 1, characterized in that the amplitude of the portion of the excitation frequency (f) of the oscillation response ($x_d$) of the contact body (6, 8) and the phase lag ($\phi$) of the portion of the excitation frequency (f) of the oscillation response ($x_d$) of the contact body (6, 8) with respect to the oscillation excitation are determined and with the knowledge of the mass ($m_d$) of the contact body (6, 8), of the mass ($m_u$) of the unbalance, of the distance ($r_u$) of the mass center of the unbalance mass ($m_u$) from the center of rotation as well as of the excitation frequency (f), the soil stiffness ($k_B$) is computed according to or with involvement of the following formula:

$$k_B = 4\pi^2 f^2 \left(m_d + \frac{m_u r_u \cos\varphi}{A_1}\right)$$

wherein f is the excitation frequency, $m_d$ is the mass of the contact body (6, 8), $m_u$ is the mass of the unbalance, $r_u$ is the distance of the mass center of the unbalance mass ($m_u$) from the center of rotation, $\phi$ is the phase lag of the portion of the excitation frequency (f) of the oscillation response ($x_d$) of the contact body (6, 8) with respect to the oscillation excitation and A1 is the amplitude of the portion of the excitation frequency (f) of the oscillation response ($x_d$) of the contact body (6, 8).

3. Method according to claim 1, characterized in that from the determined parameters (f, $\ddot{x}_d$) of the oscillation excitation of the unbalance type vibrator and/or the oscillation response of the contact body (6, 8) and from known parameters ($m_u$, $r_u$, $m_d$, $m_f$) of the acting upon arrangement (1), the ratio of the dynamic forces acting in opposite direction than the gravity forces to the weight forces acting in direction of the gravity forces is determined and in dependency of this ratio different formulas are applied for the computation of the stiffness ($k_B$) and/or the damping ($c_B$).

4. Method according to claim 3, characterized in that the amplitude of the portion of the excitation frequency (f) of the oscillation response ($x_d$) of the contact body (6, 8) and the phase lag of the portion of the excitation frequency (f) of the oscillation response ($x_d$) of the contact body (6, 8) with respect to the oscillation excitation are determined and, with the knowledge of the mass ($m_d$) of the contact body (6, 8), of the mass ($m_u$) of the unbalance, of the distance ($r_u$) of the mass center of the unbalance mass ($m_u$) from the center of rotation, of the mass ($m_f$) acting upon the roller body (6) through the chassis frame (7) as well as of the excitation frequency (f), a characteristic value ($\Phi$) is computed according to or with involvement of the following formula, which characteristic value puts into relation the dynamic forces acting in opposite direction than the gravity forces to the weight forces acting in direction of the gravity forces, $$\Phi = \frac{4\pi^2 f^2 m_u r_u \sqrt{\left(\frac{A_1}{A_0}\right)^2 + 1 + 2\left(\frac{A_1}{A_0}\right)\cos\varphi}}{(m_f + m_d)g}$$

wherein f is the excitation frequency, $m_u$ is the mass of the unbalance, $r_u$ is the distance of the mass center of the unbalance mass from the center of rotation, $\varphi$ is the phase lag of the portion of the excitation frequency (f) of the oscillation response ($x_d$) of the contact body (6, 8) with respect to the oscillation excitation, A1 is the amplitude of the portion of the excitation frequency (f) of the oscillation response ($x_d$) of the contact body (6, 8), $m_f$ is the mass acting upon the roller body (6) through the chassis frame (7) and $m_d$ is the mass of the contact body (6, 8) and $A_0$ is computed according to or with involvement of the following formula:

$$A_0 = \frac{m_u r_u}{m_d}.$$

5. Method according to claim 4, characterized in that when the characteristic value $\Phi$ is less than 1, a different formula is applied for computation of the stiffness ($k_B$) and/or the damping ($c_B$) as when the characteristic value $\Phi$ is greater than 1, and in particular that when the characteristic value $\Phi$ is less than 1, the stiffness ($k_B$) is computed according to or with involvement of the following formula:

$$k_B = 4\pi^2 f^2 \left(m_d + \frac{m_u r_u \cos\varphi}{A_1}\right)$$

and when the characteristic value $\Phi$ is greater than 1, is computed according to or with involvement of the following formula:

$$k_B = \frac{4\pi^2 f^2 (A_1 m_d + m_u r_u \cos\varphi)}{A_1 \left(1 + \cos\left\{\frac{\pi}{2}\left(\frac{\Phi - 1}{1,14}\right)^K\right\}\right)}$$

wherein f is the excitation frequency, $m_u$ is the mass of the unbalance, $r_u$ is the distance of the mass center of the unbalance mass from the center of rotation, $\varphi$ is the phase lag of the portion of the excitation frequency (f) of the oscillation response ($x_d$) of the contact body (6, 8) with respect to the oscillation excitation, A1 is the amplitude of the portion of the excitation frequency (f) of the oscillation response ($x_d$) of the contact body (6, 8), $m_d$ is the mass of the contact body (6, 8) and K is an empirical factor between 0.3 and 0.5.

6. Method according to claim 4, characterized in that the bottom plate of the vibratory plate compactor or the roller body (6, 8) of the vibratory roller (1) during the acting upon is moved along the surface (9) of the soil area.

7. Method according to claim 5, characterized in that for different characteristic values $\Phi$ different empirical factors K are applied, in particular when the characteristic value $\Phi$ is between 1 and 2, a first empirical factor K is applied and when the characteristic value $\Phi$ is greater than 2.5, another empirical factor K than the first empirical factor K is applied.

8. Method according to claim 1, characterized in that beside the portion of the excitation frequency (f) of the oscillation response ($x_d$) of the contact body (6, 8), in addition a determination for possibly present portions of other low frequencies of the excitation frequency (f) of the oscillation response ($x_d$) is performed and if such portions are determined, in dependency of the result of the determination the computation of the stiffness ($k_B$) and/or the damping ($c_B$) is influenced.

9. Method according to claim 8, characterized in that a determination for a possibly present portion of the natural frequency of a mass ($m_f$) that is coupled to the contact body (6) in a manner that it can oscillate in acting upon direction and/or for a possibly present portion of a frequency which in the sense of period duplication is not subharmonic and is lower than the excitation frequency (f) is performed and if such a portion is determined, a control intervention with respect to the unbalance type vibrator is performed and no computation of the stiffness ($k_B$) and damping ($c_B$) is performed.

10. Method according to claim 1, characterized in that the parameters (f, $\ddot{x}_d$) are continuously determined and continuously the stiffness ($k_B$) and/or damping ($c_B$) is computed therefrom.

11. Method according to claim 1, characterized in that the determined stiffness ($k_B$) and/or damping ($c_B$) is made noticeable, in particular made visually noticeable, in particular is displayed as numerical value or as bar of variable size.

12. Method according to claim 1, characterized in that by means of the bottom plate of a vibratory plate compactor or the roller body (6, 8) of a vibratory roller (1) as contact body (6, 8) it is acted upon the surface (9) of a soil (2) which in particular is compacted and/or shall be compacted, and that the soil stiffness ($k_B$) and/or damping ($c_B$) of the soil area is computed.

13. Method according to claim 12, characterized in that the soil area is compacted when by means of the bottom plate of the vibratory plate compactor or by means of the roller body (6, 8) of the vibratory roller (1) it is acted upon its surface (9).

14. Method according to claim 1, characterized in that the acting upon the contact surface (9) substantially takes place in direction of gravity forces.

15. Method according to claim 1, characterized in that as contact body (6, 8) a tool (6, 8) is employed, by means of which the area, of which the stiffness ($k_B$) and/or damping ($c_B$) shall be determined, during the acting upon the contact surface is treated, in particular is compacted.

16. Method according to claim 1, characterized in that the oscillation excitation of the unbalance type vibrator during the determination of the parameters (f, $\ddot{x}_d$) is kept substantially constant.

17. Method according to claim 1, characterized in that the acting upon the contact surface (9) by means of the contact body (6, 8) temporarily takes place in such a manner that due to the oscillation excitation of the unbalance type vibrator during the acting upon the contact surface a steady contact loss and/or no contact loss between the contact surface (9) and the contact body (6, 8) occurs.

18. Apparatus (1) for the determination of the stiffness ($k_B$) and/or damping ($c_B$) of an area of a physicalness (2), in particular for the determination of the soil stiffness ($k_B$) and/or damping ($c_B$) of a soil area, in accordance to the method according to claim 1, comprising:

a) a contact body (6, 8) for acting upon a contact surface (9) of the area, the stiffness ($k_B$) and/or damping ($c_B$) of which shall be determined in a direction substantially perpendicular to the contact surface (9), b) an in particular unregulated unbalance type vibrator, by means of which the contact body (6, 8) can be excited to perform oscillations ($x_d$) in such a manner that during the intended acting upon the contact surface (9) due to this oscillation excitation it comes or it can come to an unsteady contact loss between the contact surface (9) and the contact body (6, 8), c) measuring means for a in particular continuous determination of parameters (f, $\ddot{x}_d$) of the oscillation excitation of the unbalance type vibrator and of the oscillation response ($x_d$) of the contact body (6, 8) during an acting upon the contact surface (9) while an unsteady contact loss between the contact surface (9) and the contact body (6, 8) occurs, and d) computing means for a in particular continuous computation of the stiffness ($k_B$) and/or damping ($c_B$) of the area from the parameters (f, $x_d$) which have been determined during the acting upon the contact surface (9) while an unsteady contact loss occurred between the contact surface (9) and the contact body (6, 8).

19. Apparatus (18) according to claim 18, characterized in that the measuring means and the computing means are designed in such a manner that in addition they are suitable for a determination of the parameters (f, $\ddot{x}_d$) and for a computation of the stiffness ($k_B$) and/or damping ($c_B$) during an acting upon the contact surface (9) while a steady contact loss and/or no contact loss between the contact surface (9) and the contact body (6, 8) occurs.

20. Apparatus (1) according to claim 18, characterized in that the apparatus (1) comprises means for making the determined stiffness ($k_B$) and damping ($c_B$) visually noticeable, in particular comprises a display for displaying a numeric value representing the stiffness ($k_B$) and/or damping ($c_B$) or a bar, the lengths of which represents the stiffness ($k_B$) and damping ($c_B$).

21. Apparatus (1) according to claim 18, characterized in that the contact body (6, 8) is formed by a tool (6, 8) for treating the area of the physicalness (2).

22. Apparatus (1) according to claim 21, characterized in that the apparatus (1) is a vibratory plate compactor or a vibratory roller (1), wherein the contact body (6, 8) is formed by the bottom plate of the vibratory plate compactor or by the roller body (6, 8) of the vibratory roller (1), respectively.

23. Apparatus (1) according to claim 18, characterized in that the unbalance type vibrator is a circular vibrator or is a directional vibrator, in particular a directional vibrator with adjustable exciting force direction.

\* \* \* \* \*